US010809246B2

(12) United States Patent
Cafferty

(10) Patent No.: US 10,809,246 B2
(45) Date of Patent: Oct. 20, 2020

(54) HEMOLYSIS DETECTION METHOD AND SYSTEM

(71) Applicant: Nova Biomedical Corporation, Waltham, MA (US)

(72) Inventor: Michael Cafferty, Medford, MA (US)

(*) Notice: Subject to any disclaimer, the term of this patent is extended or adjusted under 35 U.S.C. 154(b) by 514 days.

(21) Appl. No.: 15/305,356

(22) PCT Filed: May 23, 2014

(86) PCT No.: PCT/US2014/039261
§ 371 (c)(1),
(2) Date: Oct. 20, 2016

(87) PCT Pub. No.: WO2015/178924
PCT Pub. Date: Nov. 26, 2015

(65) Prior Publication Data
US 2017/0082601 A1    Mar. 23, 2017

(51) Int. Cl.
| | | |
|---|---|---|
| G01N 33/48 | (2006.01) | |
| G01N 33/49 | (2006.01) | |
| G01N 27/06 | (2006.01) | |
| G01N 27/327 | (2006.01) | |
| G06G 7/58 | (2006.01) | |

(52) U.S. Cl.
CPC .............. *G01N 33/49* (2013.01); *G01N 27/06* (2013.01); *G01N 27/3274* (2013.01)

(58) Field of Classification Search
None
See application file for complete search history.

(56) References Cited

U.S. PATENT DOCUMENTS

| | | |
|---|---|---|
| 6,673,622 B1 | 1/2004 | Jina |
| 2003/0072549 A1 | 4/2003 | Facer et al. |
| 2013/0110405 A1 | 5/2013 | Yang et al. |

FOREIGN PATENT DOCUMENTS

| | | |
|---|---|---|
| JP | 2008-508078 A | 3/2008 |
| WO | 2006/017446 A1 | 2/2006 |
| WO | 2009-073861 A1 | 6/2009 |
| WO | 2009073861 A1 | 6/2009 |

OTHER PUBLICATIONS

J. M. Jung et al., "Determination of hematocrit using on-line conductance cell," International Journal of Heat and Mass Transfer, 2012, vol. 55, No. 7, pp. 1836-1843.
K. Cha et al., "An electronic method for rapid measurement of hematocrit in blood," Physiological Measurement, 1994, vol. 15, No. 2, pp. 129-136.
J. Wtorek et al., "The contribution of blood-flow-induced conductivity changes to measured impedance," IEEE Transactions on Biomedical Engineering, vol. 52, No. 1, pp. 41-49.
PCT International Search Report for PCT/US2014/039261 dated Feb. 12, 2015.
PCT Written Opinion of the International Searching Authority for PCT/US2014/039261 dated Feb. 12, 2015.
European Search Report in counterpart application Ser. No. EPA 14892421.1-1559, dated Oct. 20, 2017.
Japanese Office Action in counterpart application Ser. No. JPA 2017-514253, dated Mar. 13, 2018.
Canadian Office Action in counterpart application Ser. No. CA 2947000, dated Nov. 21, 2017.
Jung et al., Determination of hematocrit using on-line conductance cell, Inernational Journal of Heat and MASS Transfer, 2012, vol. 55, No. 7, pp. 1836-1843.
Russian office action is co-pending application No. 2016141161/04(065869), dated Sep. 28, 2018.
K. Cha et al., An electronic method for rapid measurement of haematocrit in blood samples, Physiol. Meas., vol. 15, pp. 129-137, Dec. 31, 1994.
Korean office action in co-pending application No. 10-2016-7032563, dated Apr. 28, 2020.

*Primary Examiner* — Eric S Dejong
(74) *Attorney, Agent, or Firm* — Sarita Pickett; Robert Deleault; Mesmer & Deleault, PLLC

(57) ABSTRACT

A hemolysis detection method and system includes measuring a conductance of a blood sample in a sample test module at a plurality of multiple-frequency AC inputs provided by a sine-wave generator module, calculating an immittance value for each of the plurality of multiple-frequency AC inputs received from a multichannel A/D converter module using a computer processing module, and subjecting each immittance value calculated to a function that maps immittance values to either lysed blood levels or hematocrit levels residing in the processing module and applying further processing residing in a memory module to produce respective percent-lysed value or hematocrit value of the blood sample.

18 Claims, 4 Drawing Sheets

HEMOLYSIS DETECTION METHOD AND SYSTEM

BACKGROUND OF THE INVENTION

1. Field of the Invention

The present invention relates generally to hemolysis. Particularly, the present invention relates to the measurement of lysed blood in a blood sample.

2. Description of the Prior Art

Analyzers that measure blood gas and electrolyte parameters of whole blood samples have been devised for some time. These analyzers can experience interferences in measuring these analytes from various factors. One factor that can influence the measurement values is when some of the blood cells have been lysed. When a cell is lysed, the cell's internal contents spill out into the plasma. Lysing occurs in clinical settings, for instance, where the blood cells have been subjected to excessive mechanical trauma such as might occur in a blood draw. Also, blood cell fragility can vary between individuals, causing occasional high-lysed cell levels for those with weak blood cells.

An example of a more serious interference problem is when the concentration of serum potassium is being measured. If a measurement sample has just a few percent of lysed cells, serum potassium can be falsely elevated over the Clinical Laboratory Improvement Amendments of 1988 regulations (the "CLIA '88") allowable error levels. This is described in an article written by M. Koseoglu et al. and titled "Effects of hemolysis interferences on routine biochemistry parameters," Biochemica Medica, (2011), 21(1), pp. 79-85, which is incorporated herein by reference. Hemolysis interference can also affect the blood analytes ammonia, alkaline phosphatase, creatinine, triglycerides, lactate dehydrogenase, phosphorus, hematocrit and uric acid, in addition to others.

Optical methods to detect the presence of hemoglobin in serum can be used to detect lysed cells. This is so since there is normally no significant hemoglobin in serum unless blood cells have been lysed. The optical absorbance of hemoglobin in serum and the optical absorbance of hemoglobin inside a whole blood cell is the same. Thus, the above-described technique of detecting the presence of hemoglobin in serum is not straightforward unless the serum has been separated from the blood cells, as with a centrifuge, filter (as described in U.S. Pat. No. 5,416,026 issued to Graham Davis, registered May 16, 1995 and assigned to I-Stat Corporation), or hematology analyzer (as described in U.S. Pat. No. 6,623,972 issued to Malin et al., registered Sep. 23, 2003 and assigned to Bayer Corporation).

U.S. Pat. No. 8,478,546 (Katsumoto et al., 2013) discloses a method for measuring physical property values of a cell based on dielectric spectroscopy and based on modeling electrical characteristics such as electric conductivity, electric permittivity, dielectric constant change, and dielectric relaxation expressions in order to obtain membrane capacitance and cytoplasmic conductivity values of the cell. Specifically, Katsumoto et al. disclose a method of utilizing dielectric spectroscopy for cells having nonisotropic shapes since the standard methods of dielectric spectroscopy cannot be applied to any cells having shapes other than a spherical shape or an ellipsoidal shape. In effect, the physical property values exhibiting the electrical characteristics such as the cell cytoplasm electric conductivity $K_i$ and the membrane capacitance $C_m$ were not determined for lysed cells in this method.

In some analyzers, electrical immittance (i.e. impedance or admittance) measurements of blood samples are used to determine hematocrit. Hematocrit is the proportion, by volume, of the blood that consists of intact red blood cells. In these analyzers, a small sample of blood (several microliters, for example) is placed between electrodes and a drive current or voltage is applied at one or two frequencies. The response current or voltage is measured and the immittance can be determined from the ratio of the drive current or voltage to the response current or voltage. Since the intact cell membrane is an insulator, the conductance at low frequencies is that of only the plasma. This conductance is inversely related to the percent hematocrit value. From these measurements the hematocrit value may be calculated. A more accurate measurement of hematocrit may be obtained by compensating for the concentration of electrolytes in the plasma by incorporating signals from an electrolyte sensor, as taught in U.S. Pat. No. 4,686,479 (Young et al. issued 1987). One example of this measurement method in use for hematocrit (Hct) levels is the Hct sensor used in an analyzer sold under the trademark pHOx® Ultra by Nova Biomedical Corporation, Waltham, Mass. (USA). This Hct sensor currently uses a single conductivity measurement at 1 kHz between two cylindrical electrodes in the fluid path of the sensor, with the electrolyte concentration compensation value provided by the Na+ sensor.

SUMMARY OF THE INVENTION

The invention to be described herein employs an immittance sensor, measuring immittance at a plurality of frequencies, to obtain the value for the level of lysed blood in a sample without the need to separate out the plasma, to use this value to correct analytes that have been affected by blood cell lysis, and to obtain a hematocrit value without the need for a separate sensor to measure the electrolyte concentration in order to compensate for it. These are very valuable features for a point-of-care blood analyzer that is in a setting where there is no available way to efficiently conduct the procedure to separate plasma from blood, where analytes affected by blood cell lysis may cause patient misdiagnosis, and where a separate electrolyte concentration sensor is not available to compensate hematocrit values.

The hemolysis sensor that is this invention is of a type similar to the hematocrit sensor just described, except that measurement of immittance at a plurality of frequencies, and subjecting these immittances to a mathematical process allows computation of the level of hemolysis of a blood sample, is employed.

It is a further characteristic of this invention that the hemolysis level measured by the invention can also be used to correct the errors in other blood analyte values that are affected by hemolysis, by applying a correction factor corresponding to the level of hemolysis and the particular analyte affected thereby.

An additional characteristic of this invention is that the immittances measured at multiple frequencies for hemolysis may also be used to calculate hematocrit by applying a second mathematical process. Methods for immittance measurement of hematocrit that use only one frequency need to be corrected for blood electrolyte concentration using a separate sensor(s). By combining the immittances of several different frequencies, additional independent measurements of the sample are made and the need for using the separate sensor(s) is eliminated.

It is an object of the present invention to provide a system and method to measure the hemolysis of a blood sample.

The present invention uses a conductivity sensor for multiple-frequency AC impedance measurements to sense impedance changes that are used to measure percent lysed blood as an analyte. These impedance measurements are then processed to yield the numerical lysed blood amount and/or percent lysed blood value.

The hemolysis value so determined may then subsequently be used in a process to correct the values of analytes affected by hemolysis. Known to be affected by hemolysis are analytes such as potassium, ammonia, alkaline phosphatase, creatinine, triglycerides, lactate dehydrogenase, phosphorus, hematocrit and uric acid, in addition to others. Correction factors or functions corresponding to both the level of hemolysis and the affected analyte can be stored in advance in the analyzer processing unit and used to change the affected analyte value back to its unaffected value. In addition, the analyzer will display a hemolysis warning to the user, and report to the user the numerical hemolysis value.

The impedance measurements used to measure the lysed blood value may additionally be used in a calculation to determine the hematocrit level. The use of a plurality of impedance measurements compensates for the interferent effects that electrolyte concentration has on the hematocrit value. The additional separate sensor inputs (such as sodium as a specific example) required to perform the electrolyte compensation are eliminated thereby. The need for a separate hematocrit sensor in the analyzer is also eliminated thereby.

A general description of the method of the present invention is now provided. A mathematical relationship between a plurality of measured immittance values (which may include either or both the magnitude and phase of each immittance) and a value of the amount of lysed blood is determined analytically, or empirically using calibration sets of data of lysed blood of a known amount. Conventional partial least squares, linear regression, linear algebra, neural networks, multivariate adaptive regression splines, or other machine learning mathematics is used with results obtained from the calibration set of data to determine the empirical relationship (or mapping function) between the immittance values and the amount of lysed blood. The relationship established is then used on future immittance measurements of unknown samples to measure their amount of lysed blood.

The measured amount of lysed blood determined has further use in this invention as an input to additional mathematical functions that produce outputs that will be used to warn the user of potential interference, correct the hemolysis interference present in the values of blood analytes such as potassium, ammonia, alkaline phosphatase, creatinine, triglycerides, lactate dehydrogenase, phosphorus, hematocrit and uric acid, in addition to others. The hemolysis amount will also be reported to the user as a hemolysis analyte value.

The impedance values measured for obtaining the lysed blood amount have further use in this invention as inputs to additional mathematical functions that produce a hematocrit measurement. A mathematical relationship between the plurality of measured immittance values (which may include either or both the magnitude and phase of each immittance) and a value of hematocrit of a blood sample is determined analytically, or empirically using calibration sets of data of blood hematocrit of a known value. Conventional partial least squares, linear regression, linear algebra, neural networks, multivariate adaptive regression splines, or other machine learning mathematics is used with results obtained from the calibration set of data to determine the empirical relationship (or mapping function) between the immittance values and the value of blood hematocrit. The relationship established is then used on future immittance measurements of unknown blood samples to measure their hematocrit.

The present invention, as above described, uses electrical immittance to calculate the percentage of cells in a blood sample that have been lysed and broken open. A broken cell membrane is no longer an insulator shielding the contents of the cell from electrical conduction at low frequencies, but becomes a kind of floating capacitor that can be charged and discharged by current passing through the broken cell membrane. By measuring electrical immittance at multiple frequencies (at least three), the present invention measures the immittance of the blood sample and the measured values are used to quantify the percentage of blood cells that have broken membranes.

No other prior art method has accomplished this where electrical immittance measurements at multiple frequencies are used to determine the degree of hemolysis of a blood sample. Also, using a determination of the hemolysis of a blood sample using immittance spectroscopy has also never been used to alert a blood analyzer user of potential interference problems with the measurements performed by the blood analyzer when determining the level of various species in the blood. For example, measuring potassium levels in the blood would be seriously affected by lysed red blood cells since the potassium concentration in the red blood cell is considerably higher than the potassium concentration in the plasma. This can also be used for a variety of analytes in the blood, such as ammonia, alkaline phosphatase, creatinine, triglycerides, lactate dehydrogenase, phosphorus, hematocrit and uric acid, in addition to others.

In addition, there may optionally include a predefined/preset limit of the hemolysis measurement that would warn a user of the blood analyzer of potential inaccurate readings of the analytes in the blood sample. Further, the measured value of the amount of lysed blood cells (i.e. the hemolysis measurement) may also be used to correct affected analyte values and reduce the errors due to the interference caused by lysed blood cells. An analyzer on configuration shall be able to include a predefined correction factor in its measurement algorithm based on the hemolysis measurement to correct the analyte readings.

The present invention achieves these and other objectives by providing in one embodiment of the present invention, a method of measuring hemolysis in a blood sample. The method includes measuring a conductance of a blood sample at a plurality of multiple-frequency AC inputs, calculating an immittance value for each of the plurality of multiple-frequency AC inputs, and subjecting each immittance value calculated to a function that maps immittance to lysed blood level to produce a percent-lysed value of the blood sample.

In another embodiment of the method, the method includes computing the function that maps immittance to lysed blood level using immittance data from a plurality of blood samples containing known but varying lysed percentages of lysed blood cells and known amounts of total hemoglobin.

In a further embodiment of the method, the method includes computing the immittance-to-lysed blood level mapping function by measuring a plurality of immittance values for the predefined conductance sensor at a plurality of predefined AC frequencies using a plurality of blood samples containing known but varying lysed percentages of lysed blood cells, and creating a calibration data set using a linear or nonlinear function to establish a relationship between a first Y matrix of known sample characteristics including percent-lysed blood cells and a second X matrix of measured immittance values at the plurality of predefined AC frequencies where the calibration data set and matrix relationship are used to determine the mapping function.

In still another embodiment of the method, the method includes subjecting each immittance value to a linear or nonlinear mapping function selected from the group consisting of partial least squares, linear regression, linear algebra, neural networks, multivariate adaptive regression splines and other machine learning mathematics.

In another embodiment of the present invention, there is disclosed a detection system that includes a blood sample test module having a pair of electrodes spaced from each other and disposed in a sample measuring chamber, a multichannel A/D converter module electrically coupled to the blood sample test module, a current sense component having a first coupling point electrically coupled to the converter module and one of the pair of electrodes of the test module, a sine-wave generator module electrically coupled between a second coupling point of the converter module and the other of the pair of electrodes where the generator module is adapted to provide a plurality of AC frequencies, and a computer processing module having a processor module, a memory module, and a function that maps immittance values to lysed blood level in the memory module that is processed by the processor module and converts a digital signal received from the converter module into a measured value where the measured value is proportional to the level of hemolysis of a sample disposed in and being measured in the test module.

In a further embodiment of the present invention, the function that maps immittance values to lysed blood is determined from a plurality of immittance values of samples having a known lysed percentage for a predefined configuration of the pair of electrodes and the sample measuring chamber.

In still another embodiment of the present invention, the function that maps immittance values to lysed blood level is based on a linear function.

In still another embodiment of the present invention, the function that maps immittance values to lysed blood level is based on a nonlinear function.

In a further embodiment of the present invention, the blood flows continuously through the sample chamber whilst the lysed blood measurement is made on-demand in an in-line configuration.

In yet another embodiment of the present invention, the blood sample test module includes two cylindrical, electrically-conductive electrodes in a fluid path having a predefined distance between the cylindrical electrodes. The electrically-conductive electrodes may be made of any electrically-conductive material including, but not limited to, gold, platinum, palladium, tungsten, stainless steel, electrically-conductive alloys, carbon, etc. A drive voltage is applied to the measuring cell, and a multichannel A/D system measures the voltage and current of the blood sample in the measuring cell. The impedance or admittance of the sample is then calculated from this information. The measurement is made at several frequencies to scan the dispersive effect of the blood cells and the broken cell membranes.

DETAILED DESCRIPTION

Figure 1:
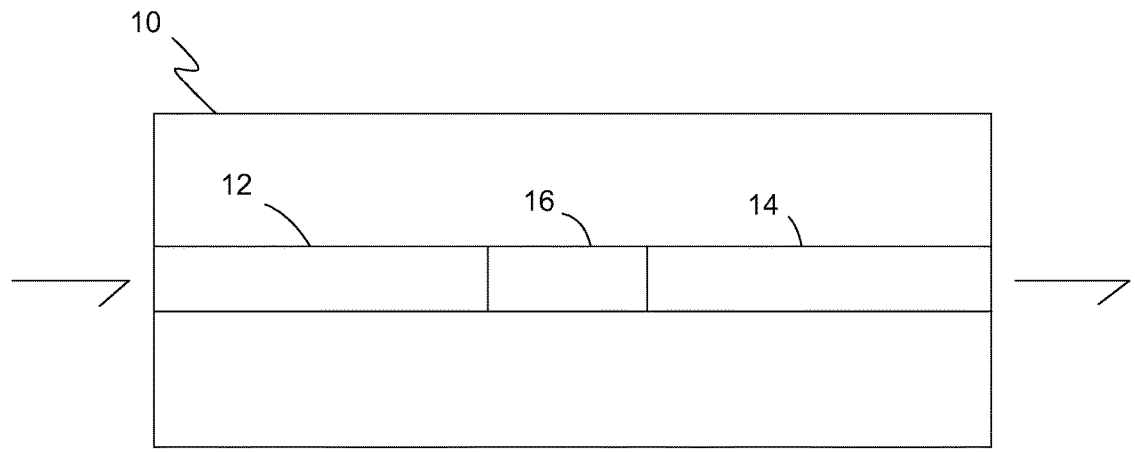
FIG. 1 is a simplified illustrated plan view of one embodiment of the present invention showing a flow path containing two cylindrical electrodes with a predefined space between the electrodes.

The present invention is illustrated in FIGS. 1-5. FIG. 1 shows one embodiment of a measuring cell 10. Measuring cell 10 forms a flow path into which a blood sample is provided for measurement. Measuring cell 10 has two tubular electrodes 12, 14 and a tubular conduit 16 having a predefined distance D between tubular electrodes 12, 14. The inside diameter and length of each tubular electrode 12, 14 is determined based on the size limit of the blood sample one wishes to require for a measurement. For example, as the inside diameter gets smaller, the smaller the total volume of sample is required to occupy the volume defined by the two tubular electrodes 12, 14 and the tubular conduit 16 between tubular electrodes 12, 14. Measurement of the immittance uses at least two electrodes, which are tubular in this preferred embodiment, but which can be of many different shapes such as rings, wires, posts, lithographically defined fingers, interdigitated electrodes, etc., without departing from the scope of this invention.

Figure 2:
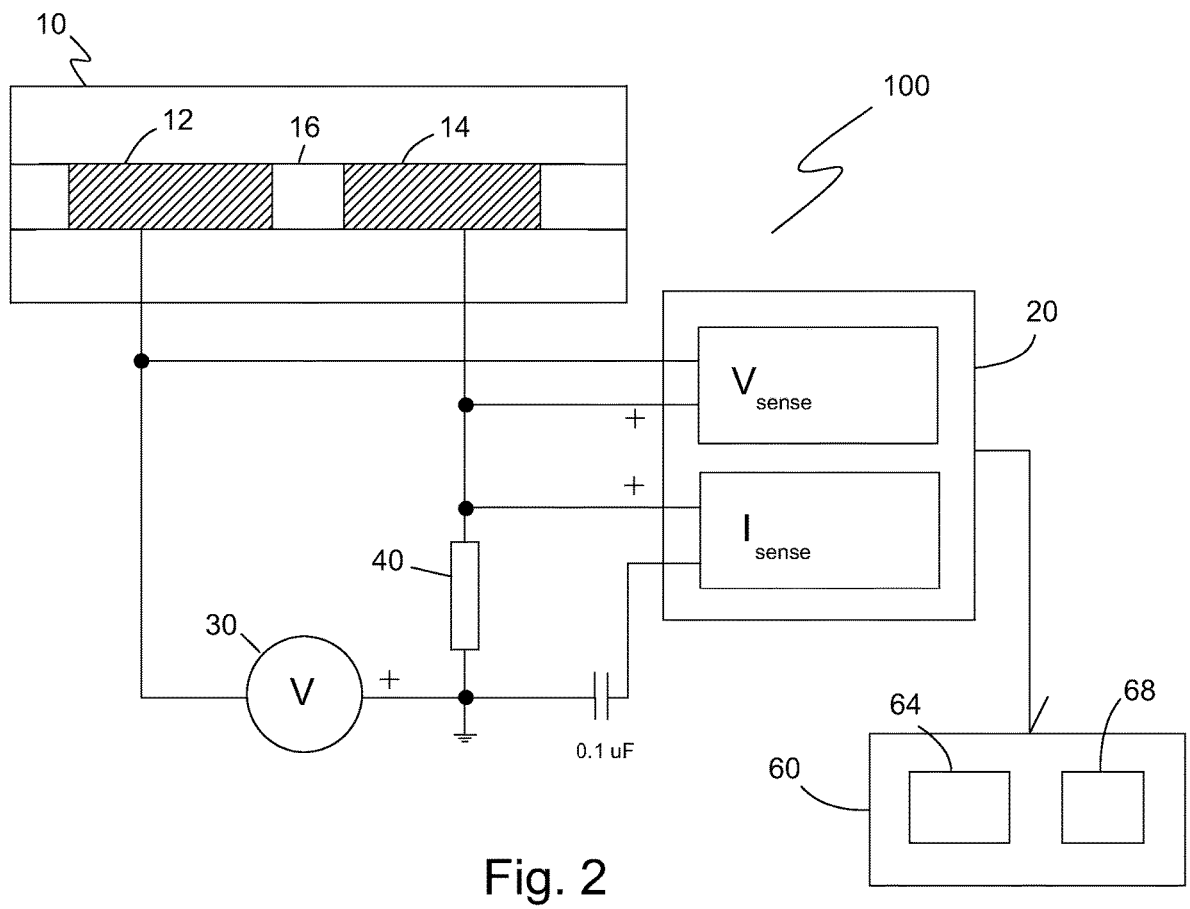
FIG. 2 is a schematic illustration of one embodiment of the present invention incorporating the two cylindrical electrodes of FIG. 1.

Turning now to FIG. 2, there is illustrated a schematic diagram of one embodiment of the hemolysis detection system 100 of the present invention. Hemolysis detection system 100 includes blood sample module 10, which includes the pair of cylindrical, electrically-conductive electrodes 12, 14 and the predefined tubular space 16 between electrodes 12, 14, a multichannel A/D converter 20, a sine wave generator 30, a current sense resistor 40, and a computer processing module 60. Computer processing module 60 includes a processor module 64, a memory module 68, and the function that maps immittance values to lysed blood and hematocrit (whilst correcting for electrolyte level) residing in memory module 68 or processor module 64.

Measurement of immittance in this embodiment uses a sine wave generator for input that produces signals at separate discrete frequencies, but other means of measuring frequency-dependent immittance may be employed such as applying an input consisting of a plurality of signals of different frequencies or broadband signals, digitizing the response and input signals, and using a Fourier-transform of the signals or other processing to obtain the frequency-dependent immittance spectrum.

Blood sample cell 10 holds the blood sample to be measured. In the example described herein, blood sample cell 10 preferably includes two 14K gold tubes as the cylindrical electrodes 12, 14 having an inner diameter (ID) of about 0.71 mm, an outer diameter (OD) of about 1.02 mm and a length of about 2.21 mm. The tubular space 16 has a length between electrodes 12, 14 of about 2.54 mm with an ID about equal to the ID of the electrodes 12, 14. Electrodes 12, 14 are mounted inside an acrylic block having the described tubular space 16. Fluids were introduced into and removed from the cell 10 through the tubular electrodes 12, 14. Saline flush solution and air was used to clean the cell 10 between samples to reduce interference between samples.

The multichannel A/D converter 20 was a Tektronics model TPS2024 oscilloscope while the sine wave generator 30 was a Tektronics model AFG3102 set to 1 V P-P output. The current sense resistor 40 was a resistor having a resistance value of 12.41K ohms. The oscilloscope digitized the measured waveforms (voltage sine waves) and a computer was used to calculate the RMS amplitude information of the following signals: 1) voltage across the sample cell ($V_{sense}$), and 2) voltage across the current sense resistor ($I_{sense}$) (which is proportional to the current through the sample cell). The oscilloscope also calculated the DC mean value of the time-domain voltage-multiplied-by-current signal ($MV_{sense}I_{sense}$). Data were collected at frequencies of 100 kHz, 500 kHz, 1 MHz, and 2 MHz.

Calculations:

The data collected was used to determine admittance values for the blood samples measured at the plurality of AC frequencies. The admittance Y was calculated from the oscilloscope measurements at each frequency (f) using the following equations.

$$\text{Mag}(f) = R_1 \cdot V_{sense}(f)/I_{sense}(f) \quad \text{(Eq. 1)}$$

$$\text{Pha}(f) = \arccos(MV_{sense}I_{sense}(f)/V_{sense} \cdot I_{sense}(f)) \quad \text{(Eq. 2)}$$

$$Y(f) = 1/(\text{Mag}(f) \cdot \cos(\text{Pha}(f)) + i \cdot M(f) \cdot \sin(\text{Pha}(f))) \quad \text{(Eq. 3)}$$

where Y(f) is the complex admittance value calculated at the given frequency
- Mag(f) is the magnitude of the impedance of the sample
- Pha(f) is the phase of the impedance of the sample
- $R_1$ is the sense resistor value
- $V_{sense}(f)$ is the voltage across the cell at the given frequency
- $I_{sense}(f)$ is the voltage across the sense resistor $R_1$ at the given frequency
- $MV_{sense}I_{sense}$ (f) is the calculated DC mean voltage-multiplied-by-current signal at the given frequency
- i is the positive root of the square root of −1

Prediction Model:

The next step in the calculation is to create a prediction model. Using an initial calibration data set, the calibration sequence of a machine learning algorithm establishes a relationship between a matrix of known sample characteristics (the H matrix) and a matrix of measured admittance values at several frequencies and potentially other measured values (the X matrix). The real and imaginary parts of the admittance at each frequency may be considered as independent values and used separately as well as together. Once this relationship is established, it is used by analyzers to predict the unknown H values from new measurements of X on samples. The calibration set H matrix is built up as follows from the known values of the calibration sample set of n blood samples:

$$H = \begin{bmatrix} \% \ Lysed_1 & \% \ Hct_1 \\ \% \ Lysed_2 & \% \ Hct_2 \\ \% \ Lysed_n & \% \ Hct_n \end{bmatrix}$$

where % Lysed is the percentage of cells lysed, and
% Hct is the percent volume of hematocrit.

Although the % Hct may be left out without adversely affecting the usefulness of the present invention, it is noted that in addition to extracting the % Lysed value, the calibration set will be structured to extract the % Hct from the measured data as well. The immittance measurements can optionally be used to determine % Hct at the same time, providing an additional useful output.

The X matrix is structured as follows:

$$X = \begin{bmatrix} \text{Imag}(Y_1(f_1)) & \text{Imag}(Y_1(f_2)) & \text{Imag}(Y_1(f_3)) & \text{Imag}(Y_1(f_4)) & \text{Re}(Y_1(f_3)) & \text{Re}(Y_1(f_4)) & tHb_1 \\ \text{Imag}(Y_2(f_1)) & \text{Imag}(Y_2(f_2)) & \text{Imag}(Y_2(f_3)) & \text{Imag}(Y_2(f_4)) & \text{Re}(Y_2(f_3)) & \text{Re}(Y_2(f_4)) & tHb_2 \\ \dots \\ \text{Imag}(Y_n(f_1)) & \text{Imag}(Y_n(f_2)) & \text{Imag}(Y_n(f_3)) & \text{Imag}(Y_n(f_4)) & \text{Re}(Y_n(f_3)) & \text{Re}(Y_n(f_4)) & tHb_n \end{bmatrix}$$

where: $f_1$, $f_2$, $f_3$, $f_4$ are 100 kHz, 500 kHz, 1 MHz, and 2 MHz, respectively.
Imag represents taking the imaginary part of the complex immittance.
Re represents taking the real part of the complex immittance.

The matrix X includes contributions from the real and imaginary parts of the admittance at the various frequencies. Optionally, other measured values besides admittance may be included to reduce the effects of interferents and increase the accuracy of the measurement. Since the total hemoglobin (tHb) level is a potential interferent to the measurement, it is included in the matrix, in units of g/dL. In an analyzer, this value is determined by separate sensor(s), such as an oximeter, and may be made available at the time of measurement. The scope of the invention includes optionally adding other measurements to the calculation to reduce these interferent effects. Supplying the value of tHb also allows the mathematics to compute the lysed blood level in percentage terms.

Once these matrices are formed, they are used as the calibration set and the mapping function is computed according to the procedures particular to the machine learning algorithm chosen.

As described previously, conventional partial least squares, linear regression, linear algebra, neural networks, multivariate adaptive regression splines, kernel-based orthogonal projection to latent structures, or other machine learning mathematics is used with results obtained from the calibration set of data to determine the empirical relationship (or mapping function) between the immittance values and the amount of lysed blood. Typically, a mathematics package is used to generate the results where the package generally has options to select one of the machine learning mathematics known to those skilled in the art. Various mathematics packages exist and include, but are not limited to, Matlab by MatWorks of Natick, Mass., "R" by R Project for Statistical Computing available over the Internet at www.r-project.org, Python from Python Software Foundation and available over the Internet at www.python.org in combination with Orange data mining software from Orange Bioinformatics available over the Internet at orange.biolab.si, to name a few.

It will be shown that the method of Kernel-Based Orthogonal Projection to Latent Structures (KOPLS) may be used as one type of machine learning algorithm to generate the mapping function. An explanation and description of KOPLS is best exemplified by the following references: Johan Trygg and Svante Wold. "*Orthogonal projections to latent structures (O-PLS)*." J. Chemometrics 2002; 16:119-128; Mattias Rantalainen et al. "*Kernel-based orthogonal projections to latent structures (K-OPLS)*." J. Chemometrics 2007; 21:376-385; and Max Bylesjö et al. "*K-OPLS package: Kernel-based orthogonal projections to latent structures for prediction and interpretation in feature space.*" BMC Bioinformatics 2008, 9:106, which references are incorporated herein by reference. The kernel-based mathematics is useful in handling non-linear behavior in systems by using a kernel function to map the original data to a higher order space. Although any of the previously described machine learning mathematics may be used to enable one of ordinary skill in the art to practice the present invention, KOPLS has an additional advantage over other calculations such as, for example, conventional partial least squares because it can not only establish a relationship between quantified variations and analyte values to be determined, but can also remove unquantitated yet consistently present variation in the original data. These unquantitated variations might be due to sample characteristics, analyzer baseline variations, drifts, etc.

Using an initial training data set, the KOPLS model establishes a relationship (mapping function) between the matrix of known sample characteristics (the H matrix), and a matrix of measured admittance values at several frequencies and potentially other measured values (the X matrix) as processed through a kernel function as specified by the KOPLS method. The real and imaginary parts of the admittance at each frequency may be considered as independent values and used separately as well as together. Once the KOPLS coefficients of this relationship are established, they are used with the kernel function by analyzers to predict the unknown H values from new measurements of X on samples.

The kernel function used in this example is a simple linear kernel function described in the Mattias Rantalainen et al. reference listed above and represented by the following equation:

$$\kappa(X,X) = \langle X,X \rangle$$

where the matrix of measured values X is put into the kernel function and subjected to further processing as specified in the cited KOPLS references above (incorporated by reference) for creating the KOPLS training coefficients.

Once the set of training coefficients, or mapping function, is established, it is used to predict the % Lysed value of a blood sample from future measurements. A single-row X matrix is created from the new measurements, then the value from this single-row X matrix is put through the kernel and mapping functions to produce the % Lysed value according to the procedures necessary for the mapping function used according to the KOPLS procedures described in detail in the KOPLS references disclosed previously.

The data collected from the blood samples described above were put through the KOPLS method in a cross-validation process. Cross-validation is a process for using a data set to test a method. Several data rows are set aside and the rest are used to create a mapping function. The set-aside values are then used as "new" measurements and their H matrix values calculated. This process is repeated by setting aside other measured values and computing another mapping function. By plotting the known values of the blood data vs. the calculated, the effectiveness of the method may be ascertained by inspecting the plot.

Figure 3:
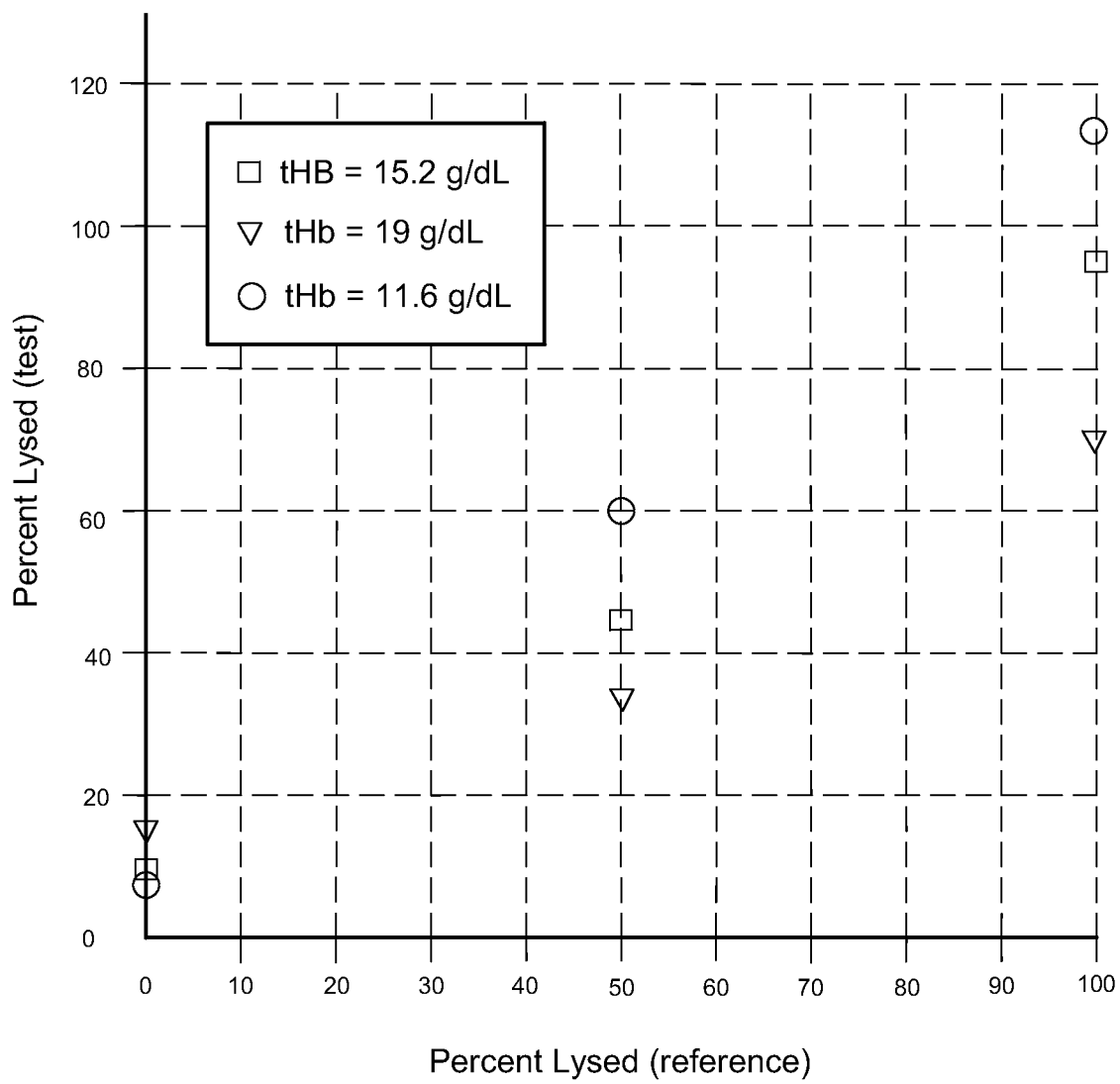
FIG. 3 is a graphic illustration showing a comparison of hemolysis measurement versus known lysed percentage.

Turning now to FIG. 3, there is illustrated a plot of the results comparing the hemolysis measurement of samples (test) versus the known lysed percentage of the samples (reference) using the KOPLS method. The set of blood data used samples where the percent lysed samples were 0%, 50% and 100% lysed. The test also included samples having varying amounts of total hemoglobin, varying percentage of hematocrit, and varying electrolyte levels. Three levels of total hemoglobin (tHb) were used. The hemoglobin values were 11.6 g/dL, 15.2 g/dL and 19 g/dL. The horizontal axis has units representing the percent lysed of the reference samples and the vertical axis has units representing the percent lysed of the measured test samples. As can be seen from the plot, the method of determining hemolysis of a sample is effective.

Figure 4:
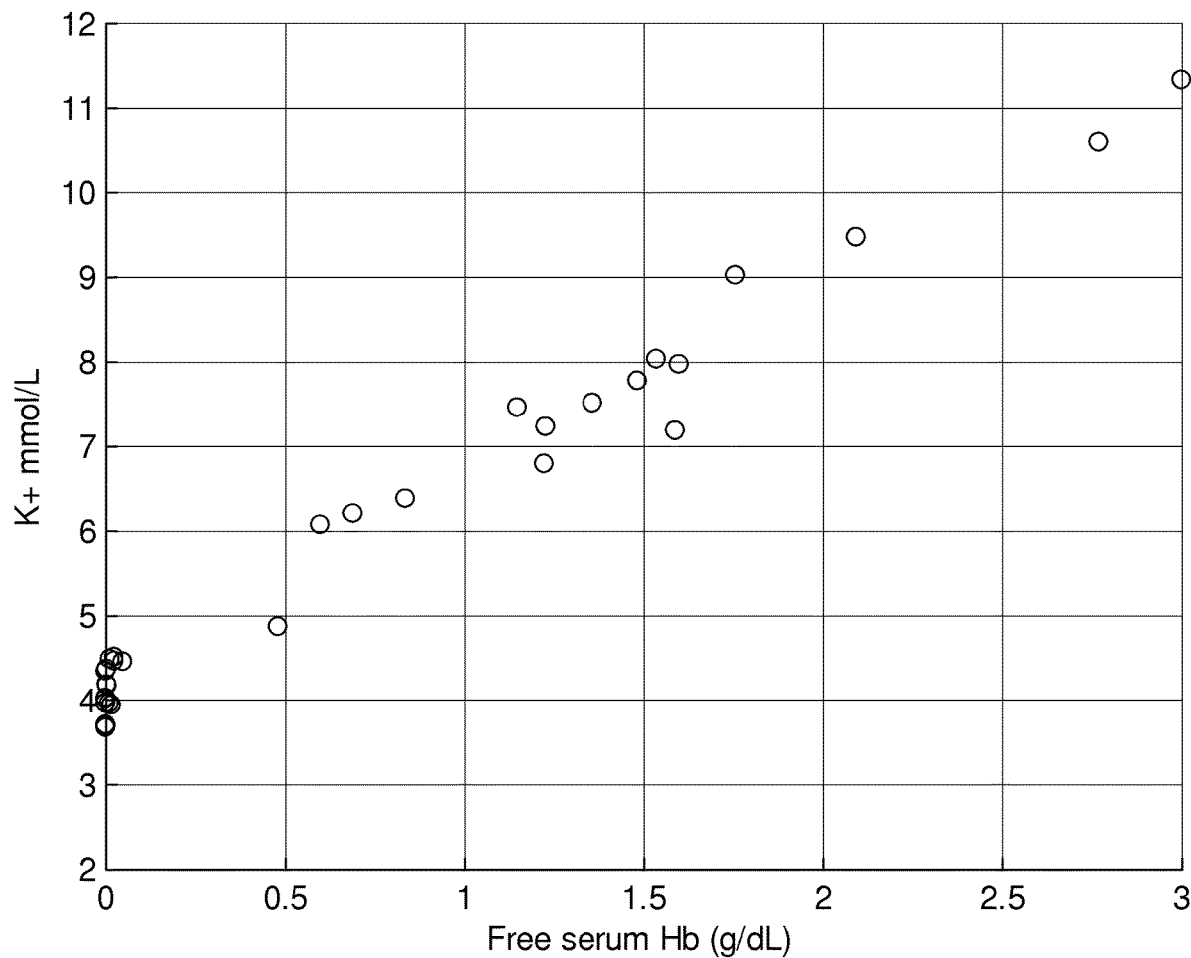
FIG. 4 is a graphic illustration showing a comparison of serum potassium ion (K+) measurement versus free serum hemoglobin (Hb).

Turning now to FIG. 4, there is illustrated a plot of the results comparing the excess serum potassium measurement of the samples versus the known lysed blood amount of the samples as represented by free serum hemoglobin. The interferent effect on analytes caused by hemolysis is proportional to the amount of hemoglobin freed by lysed blood cells. Once the amount of free serum hemoglobin is known, by measurement of percent lysed blood multiplied by total hemoglobin, the amount of potassium in excess over normal levels (where free serum hemoglobin is zero) can be determined from the data in FIG. 4 by following the trend of increase over the normal level as a function of free serum hemoglobin. This excess level is subtracted from the uncorrected potassium level measured for the sample and the corrected potassium value is reported to the user.

Figure 5:
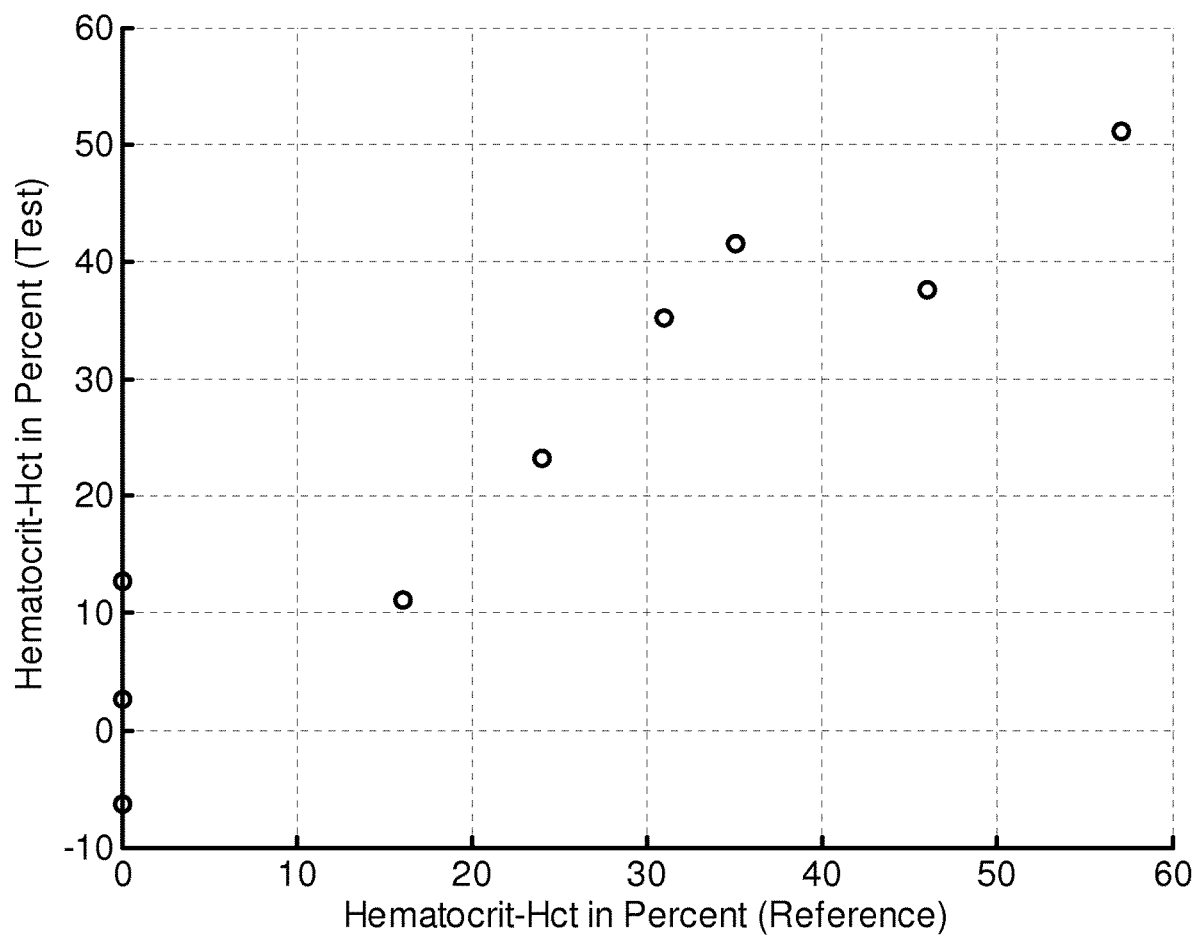
FIG. 5 is a graphic illustration showing a comparison of hematocrit measurement versus known hematocrit.

Turning now to FIG. 5, there is illustrated a plot of the results comparing the measured % Hct (hematocrit) of the samples (test) versus the known % Hct of the samples (reference). As can be seen from the plot, the method of determining % Hct of a sample is effective.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A method of measuring hemolysis or hematocrit in a blood sample, the method comprising:
    a. disposing the blood sample in a blood sample module having multiple electrodes spaced from each other by a conduit, the multiple electrodes and the conduit forming a flow path;
    b. measuring an immittance value of the blood sample, the measuring being done at each of at least three multiple-frequency AC inputs; and
    c. subjecting each immittance value measured in step b to a mapping function selected from the group consisting of neural networks and kernel-based orthogonal projection to latent structures, wherein the mapping function is one of the following:
        a function (1) that maps immittance values to lysed blood levels and determining the level of lysed blood in the sample; or
        a function (2) that maps immittance values to hematocrit levels and determining the level of hematocrit in the sample while compensating for the electrolyte level of the sample.

2. The method of claim 1 further comprising computing (1) the function that maps immittance values to lysed blood levels using a plurality of blood samples containing known but varying lysed percentages of lysed blood cells or (2) the function that maps immittance values to hematocrit levels while compensating for the electrolyte level of the sample using a plurality of blood samples containing known but varying percentages of hematocrit and varying electrolyte levels.

3. The method of claim 2 wherein the step of determining the function that maps immittance values to either lysed blood or hematocrit, the step further comprising:
   measuring a plurality of immittance values for a predefined conductance sensor at least three AC frequencies using a plurality of blood samples containing known but varying lysed percentages of lysed blood cells or known but varying percentages of hematocrit and varying electrolyte levels; and
   creating a calibration data set (1), when the blood sample contains lysed blood cells, using a function that maps immittance values to lysed blood levels to establish a relationship between a first H matrix of known sample characteristics including percent-lysed blood cells and a second X matrix of measured immittance values at the at least three predefined AC frequencies wherein the calibration data set and matrix relationship are used in computation of the function that maps immittance values to lysed blood levels or (2), when the blood sample contains varying percentages of hematocrit and varying electrolyte levels, using a function that maps immittance values to hematocrit levels while compensating for electrolyte levels to establish a relationship between a first H matrix of known sample characteristics including percent-hematocrit and a second X matrix of measured immittance values at the at least three predefined AC frequencies wherein the calibration data set and matrix relationship are used in computation of the function that maps immittance values to hematocrit levels while compensating for the electrolyte levels.

4. The method of claim 1 wherein the mapping function is created from a predefined machine learning mathematics.

5. The method of claim 1 further comprising using the level of lysed blood to correct the effect of hemolysis interference on other blood analytes.

6. The method of claim 1 further comprising using the level of lysed blood to correct the effect of hemolysis interference on potassium.

7. The method of claim 1 further comprising using the plurality of immittance values in a computation to produce the level of hematocrit of a blood sample.

8. The method of claim 1 further comprising flowing blood through a blood sample module having an in-line configuration.

9. A hemolysis and/or hematocrit detection system comprising:
   a blood sample module having multiple electrodes spaced from each other by a conduit, the multiple electrodes and the conduit forming a flow path;
   an A/D converter module electrically coupled to the blood sample module;
   a current sense component having a first coupling point and a second coupling point wherein the first coupling point is electrically coupled to the converter module and one of the multiple electrodes of the blood sample module;
   a sine-wave generator electrically coupled between the second coupling point of the converter module and the other one of the multiple electrodes wherein the sine-wave generator is adapted to provide a plurality of AC frequencies; and
   a computer processing module having a processor module, a memory module, and one of the following:
      a function (1) that maps immittance values to lysed blood levels in the memory module that is processed by the processor module and converts a digital signal received from the converter module into a measured value wherein the measured value is proportional to a percentage of hemolysis of a sample disposed in and being measured in the blood sample module at each of at least three multiple-frequency AC inputs, wherein the function (1) is selected from the group consisting of neural networks and kernel-based orthogonal projection to latent structures, or
      a function (2) that maps immittance values to hematocrit levels while compensating for the electrolyte levels in the memory module that is processed by the processor module and converts a digital signal received from the converter module into a measured value wherein the measured value is proportional to a percentage of hematocrit of a sample disposed in and being measured in the blood sample module at each of at least three multiple-frequency AC inputs, wherein the function (2) is selected from the group consisting of neural networks and kernel-based orthogonal projection to latent structures.

10. The system of claim 9 wherein the function that maps immittance values to lysed blood levels is generated from a plurality of immittance values of samples having a known lysed percentage for a predefined configuration of at least a pair of multiple electrodes and the conduit, and wherein the function that maps immittance values to hematocrit levels while compensating for the electrolyte level is generated from a plurality of immittance values of samples having a known but varying percentage hematocrit and varying levels of electrolyte for a predefined configuration of the pair of multiple electrodes and the conduit, wherein each of the plurality of immittance values is measured using at least three different AC inputs.

11. The system of claim 10 wherein the pair of multiple electrodes are tubular electrodes defining a portion of the flow path.

12. The system of claim 9 wherein each of the multiple electrodes are made of a material selected from the group consisting of gold, platinum, palladium, tungsten, stainless steel, electrically conductive alloys, and carbon.

13. The system of claim 9 wherein the current sensing component is a resistor.

14. The system of claim 9 wherein the electrodes are interdigitated.

15. The system of claim 9 wherein the level of lysed blood is used in a calculation to remove the effect of hemolysis interference on other blood analytes.

16. The system of claim 9 wherein the level of lysed blood is used in a calculation to remove the effect of hemolysis interference on potassium.

17. The method of claim 10 wherein the plurality of immittances is additionally used in a computation to produce the level of hematocrit of a blood sample.

18. The system of claim 9 wherein blood flows through the multiple electrodes and the conduit in an in-line configuration.

* * * * *